US010813661B2

(12) United States Patent
Smith et al.

(10) Patent No.: US 10,813,661 B2
(45) Date of Patent: Oct. 27, 2020

(54) ULTRASONIC TREATMENT DEVICES AND SYSTEMS

(71) Applicant: Boston Scientific Scimed, Inc., Maple Grove, MN (US)

(72) Inventors: Paul Smith, Smithfield, RI (US); Ray Tong, Foxboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 135 days.

(21) Appl. No.: 15/332,303

(22) Filed: Oct. 24, 2016

(65) Prior Publication Data
US 2017/0112524 A1    Apr. 27, 2017

Related U.S. Application Data

(60) Provisional application No. 62/245,532, filed on Oct. 23, 2015.

(51) Int. Cl.
*A61B 17/32* (2006.01)
*A61B 17/22* (2006.01)
(Continued)

(52) U.S. Cl.
CPC .. *A61B 17/320068* (2013.01); *A61B 17/2202* (2013.01); *A61N 7/00* (2013.01); *A61B 1/00137* (2013.01); *A61B 17/320092* (2013.01); *A61B 2017/0034* (2013.01); *A61B 2017/00199* (2013.01); *A61B 2017/00287* (2013.01); *A61B 2017/00296* (2013.01); *A61B 2017/00402* (2013.01); *A61B 2017/00415* (2013.01); *A61B 2017/22021* (2013.01);
(Continued)

(58) Field of Classification Search
CPC ........ A61B 17/2202; A61B 17/320016; A61B 17/320068; A61B 17/320092; A61B 2017/00269; A61B 2017/0046; A61B 2017/22008; A61B 2017/2927; A61B 2017/2929; A61B 2017/320072; A61B 18/1492; A61B 2017/320071
USPC .......................................................... 310/311
See application file for complete search history.

(56) References Cited

U.S. PATENT DOCUMENTS

| 4,530,138 | A | * | 7/1985 | Ritter | .................... B06B 1/0618 156/285 |
| 5,349,940 | A | | 9/1994 | Takahashi et al. | |

(Continued)

*Primary Examiner* — Kathleen S Holwerda
*Assistant Examiner* — Kankindi Rwego

(57) ABSTRACT

In one aspect, the present disclosure pertains to ultrasonic treatment devices that comprise: (a) a flexible elongate body having a proximal end and a distal end, the flexible elongate body being configured for insertion to a target site within a patient; (b) an effector assembly disposed at the distal end of the flexible elongate body, the effector assembly comprising a piezoelectric transducer and an end effector; and (c) flexible electrical conductors in electrical communication with the piezoelectric transducer, the flexible electrical conductors extending along a length of the flexible elongate body, wherein transference of electrical energy to mechanical motion takes place via the piezoelectric transducer at the target site. Other aspects of the present disclosure pertain to systems employing such ultrasonic treatment devices and methods of treatment using such ultrasonic treatment devices.

18 Claims, 7 Drawing Sheets

(51) Int. Cl.
*A61N 7/00* (2006.01)
*A61B 1/00* (2006.01)
*A61B 17/00* (2006.01)
*A61B 17/29* (2006.01)
*A61B 18/00* (2006.01)

(52) U.S. Cl.
CPC ............. *A61B 2017/2927* (2013.01); *A61B 2017/320088* (2013.01); *A61B 2018/00607* (2013.01)

(56) References Cited

U.S. PATENT DOCUMENTS

| | | |
|---|---|---|
| 2005/0049525 A1 | 3/2005 | Yamada et al. |
| 2005/0272976 A1 | 12/2005 | Tanaka et al. |
| 2006/0066181 A1* | 3/2006 | Bromfield ............ H01L 41/047 310/363 |
| 2007/0038157 A1 | 2/2007 | Yamada et al. |
| 2008/0214967 A1* | 9/2008 | Aranyi ............ A61B 17/320068 601/3 |
| 2009/0066192 A1* | 3/2009 | Taki ............... A61B 17/320068 310/354 |
| 2009/0216157 A1 | 8/2009 | Yamada |
| 2012/0037390 A1* | 2/2012 | Bao ................. B23B 37/00 173/113 |
| 2013/0144186 A1 | 6/2013 | Furlong |
| 2014/0005701 A1 | 1/2014 | Olson et al. |
| 2014/0005702 A1 | 1/2014 | Timm et al. |

* cited by examiner

ULTRASONIC TREATMENT DEVICES AND SYSTEMS

PRIORITY

This application claims the benefit of priority under 35 U.S.C. § 119 to U.S. Provisional Patent Application Ser. No. 62/245,532, filed Oct. 23, 2015, which is incorporated by reference in its entirety and for all purposes.

BACKGROUND

For many years, ultrasonic cutting devices have been used in laparoscopic procedures. These devices employ a piezoelectric transducer that generates ultrasonic waves that are used to move a distal attachment back and forth at ultrasonic frequencies.

Ultrasonic waves produced by a transducer, however, do not travel well through curved shafts. Consequently, laparoscopic devices utilizing piezoelectric transducers frequently use a transducer attached to the operator handle, with the piezoelectric transducers connected to the distal attachment along a straight ultrasonic waveguide.

SUMMARY

The present disclosure provides an ultrasonic treatment device design in which a piezoelectric transducer is configured to operate at a distal end of a tortuous path traversed by an endoscope.

In some aspects, the present disclosure pertains to ultrasonic treatment devices that comprise: (a) a flexible elongate body having a proximal end and a distal end, the flexible elongate body being configured for insertion to a target site within a patient; (b) an effector assembly disposed at the distal end of the flexible elongate body, the effector assembly comprising a piezoelectric transducer and an end effector; and (c) flexible electrical conductors in electrical communication with the piezoelectric transducer, the flexible electrical conductors extending along a length of the flexible elongate body. Transference of electrical energy to mechanical motion in the ultrasonic treatment devices takes place via the piezoelectric transducer at the target site.

In certain embodiments, the ultrasonic treatment devices may be ultrasonic cutting device.

In certain embodiments, which may be used in combination with any of the above aspects and embodiments, the end effector may be selected from a rod, a ball, a hook and a sharp cutting tool.

In certain embodiments, which may be used in combination with any of the above aspects and embodiments, the effector assembly may further comprise a piezoelectric amplifier disposed between and mechanically linking the piezoelectric transducer and the end effector.

In certain embodiments, which may be used in combination with any of the above aspects and embodiments, the effector assembly may further comprise an actuatable arm configured to press tissue against the end effector. In such embodiments, the actuatable arm may be configured to pivot via hinged joints disposed in a housing that houses the piezoelectric transducer. In such embodiments, the end effector may be rotatable independent of the actuatable arm.

In certain embodiments, which may be used in combination with any of the above aspects and embodiments, the ultrasonic treatment devices may be provided with a generator for sending electrical signals to the piezoelectric transducer.

In certain embodiments, which may be used in combination with any of the above aspects and embodiments, the flexible elongate body may be configured for insertion through a working channel of an endoscope.

In certain embodiments, which may be used in combination with any of the above aspects and embodiments, the flexible elongate body may be an endoscope body. In such embodiments, the effector assembly may be inserted into a lumen at a distal end of the endoscope in a back-fed attachment, or the effector assembly may be attached to a distal end of the endoscope as a cap. In such embodiments, the flexible electrical conductors may be disposed within a lumen of the endoscope body or the flexible electrical conductors may be disposed alongside the endoscope body, among other possibilities.

In certain embodiments, which may be used in combination with any of the above aspects and embodiments, the effector assembly may comprise (i) an articulation portion positioned at the distal end of the flexible elongate body, and (ii) an articulation control that extends proximally from the articulation portion and the effector assembly. In such embodiments, the articulation portion may be selected from a joint, a link, a flexible segment, a corrugated segment, a slotted segment or a pre-bent segment with shape memory, among other possibilities. In such embodiments, the articulation control may be selected from a wire, a rod and a sheath, among other possibilities.

Other aspects of the present disclosure pertain to endoscopic systems that comprise: (a) a control unit comprising an electrical generator that is configured to generate ultrasonic control signals, and (b) an ultrasonic treatment device in accordance with any of the above aspects and embodiments.

In certain embodiments, the control unit may further comprise a user interface.

In certain embodiments, which may be used in combination with any of the above aspects and embodiments, the control unit may further comprise a hand-operated or foot-operated activation mechanism that is configured to activate and deactivate the piezoelectric transducer.

Still other aspects of the present disclosure pertain to methods of treatment using ultrasonic treatment devices and systems in accordance with any of the above aspects and embodiments.

DETAILED DESCRIPTION

Figure 1A:
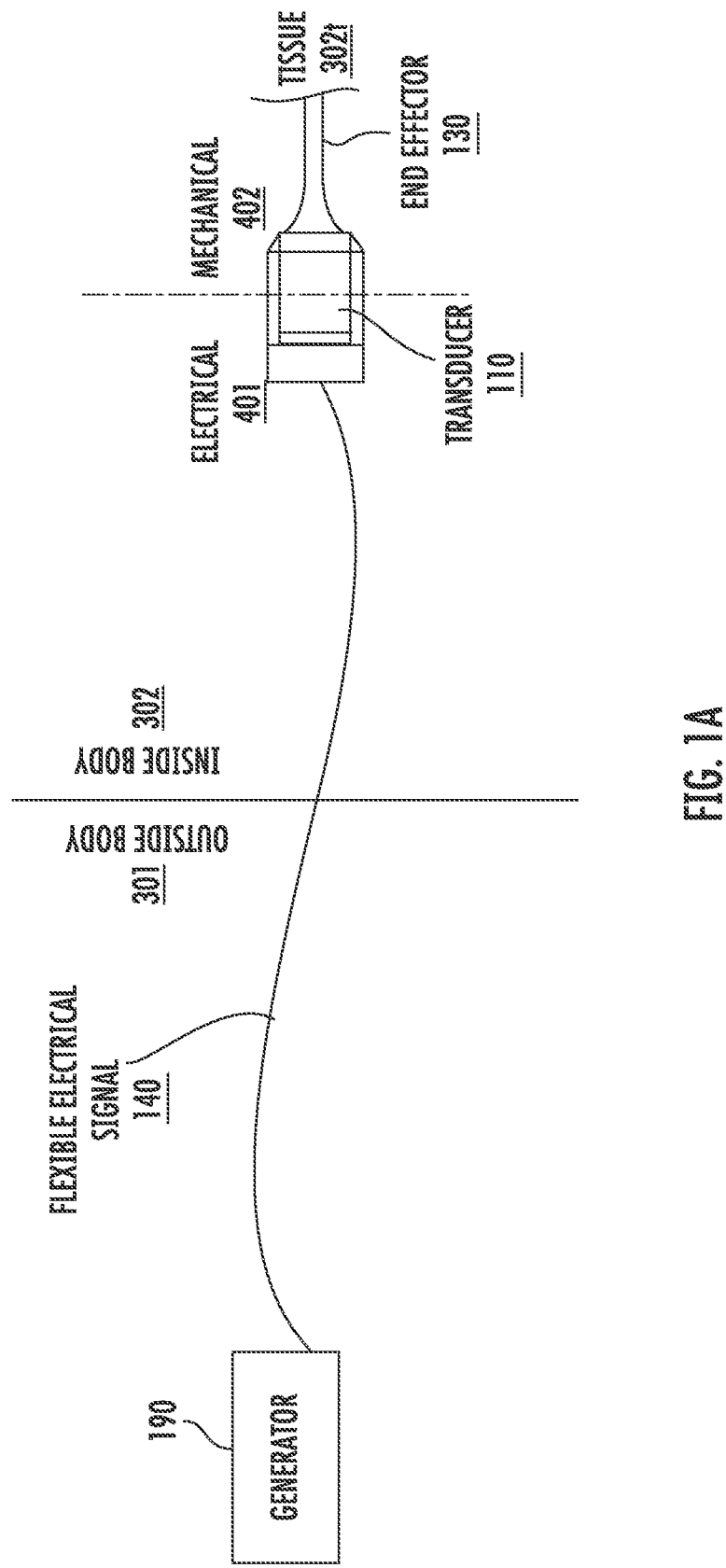
FIG. 1A is a schematic diagram of an endoscopic system, in accordance with the present disclosure.

This ultrasonic cutting method provides unique cutting and coagulation properties that, in the present disclosure, are used in endoscopy. In various embodiments, and with reference to the schematic diagram of FIG. 1A, the present disclosure provides an ultrasonic treatment device design in which a piezoelectric transducer 110 operates at a distal end of a path traversed by an endoscope. Unlike many other ultrasonic surgical tools, the transducer 110 is not held by the operator outside the patient body 310, but instead is inserted into the patient's body 302, along with an end effector 130, to tissue 302t at a target site. It is at the target site 302t that a transference from electrical energy 401 to mechanical energy 402 takes place via the transducer 110. The mechanical energy is then used to treat tissue 302t via the end effector 130. In various embodiments, the transducer 110 is connected to a generator 190 along a flexible electrical signal path 140, which allows the transducer 110 to be operated at the end of a flexible elongate body (e.g., a flexible hollow shaft, an endoscope, etc.), which can navigate tortuous body lumens within the patient.

As previously indicated, in some aspects, the present disclosure provide ultrasonic treatment devices (as opposed to ultrasonic diagnostic devices, such as ultrasonic imaging devices) which comprise: (a) flexible elongate body, (b) an effector assembly disposed at the distal end of the flexible elongate body, the effector assembly comprising a piezoelectric transducer and an end effector, (c) a plurality of flexible electrical conductors extending along a length of the flexible elongate body, the electrical conductors being configured to provide at least a portion of a conductive path between the piezoelectric transducer and a control unit.

Piezoelectric transducers for use in the present disclosure may be formed from any material that can be driven to oscillate using a drive signal output by generator and are commonly formed from piezo-ceramic materials, among other possibilities. Typically, the piezoelectric transducers include a stack of piezoelectric disks, which are wired to a circuit. The stack of disks may be pre-compressed to reduce the amount of energy required to activate the piezoelectric disks. As an alternating current is passed through these disks, the stack expands and contracts. This expansion and contraction drives the end effector at an ultrasonic frequency.

End effectors for use in conjunction with the present disclosure vary widely and include sharp cutting tools as well as rods, among many other possibilities. The ultrasonic vibration transferred to the end effector from the transducer can give these tools enhanced cutting and coagulation properties.

In some embodiments, one or more optional amplification devices may be placed between the piezoelectric transducer and end effector to increase the oscillation displacement amplitude of the output of the transducer. For example, a tapered metal member (sometimes referred to as an acoustic waveguide, acoustic horn or ultrasonic horn) may be used to augment the oscillation displacement amplitude provided by the ultrasonic transducer. The tapered metal member typically has a longitudinal cross-section profile that converges towards the output end, resulting in a longitudinal oscillation amplitude that increases towards the output end as the area of its transverse cross-section decreases. Different amplifier geometries can be used to produce different effects.

In various embodiments, the effector assembly may be disposed at the end of a flexible elongate body, and the effector assembly and flexible elongate body may both be dimensioned to be inserted through the working channel of an endoscope.

Figure 1B:
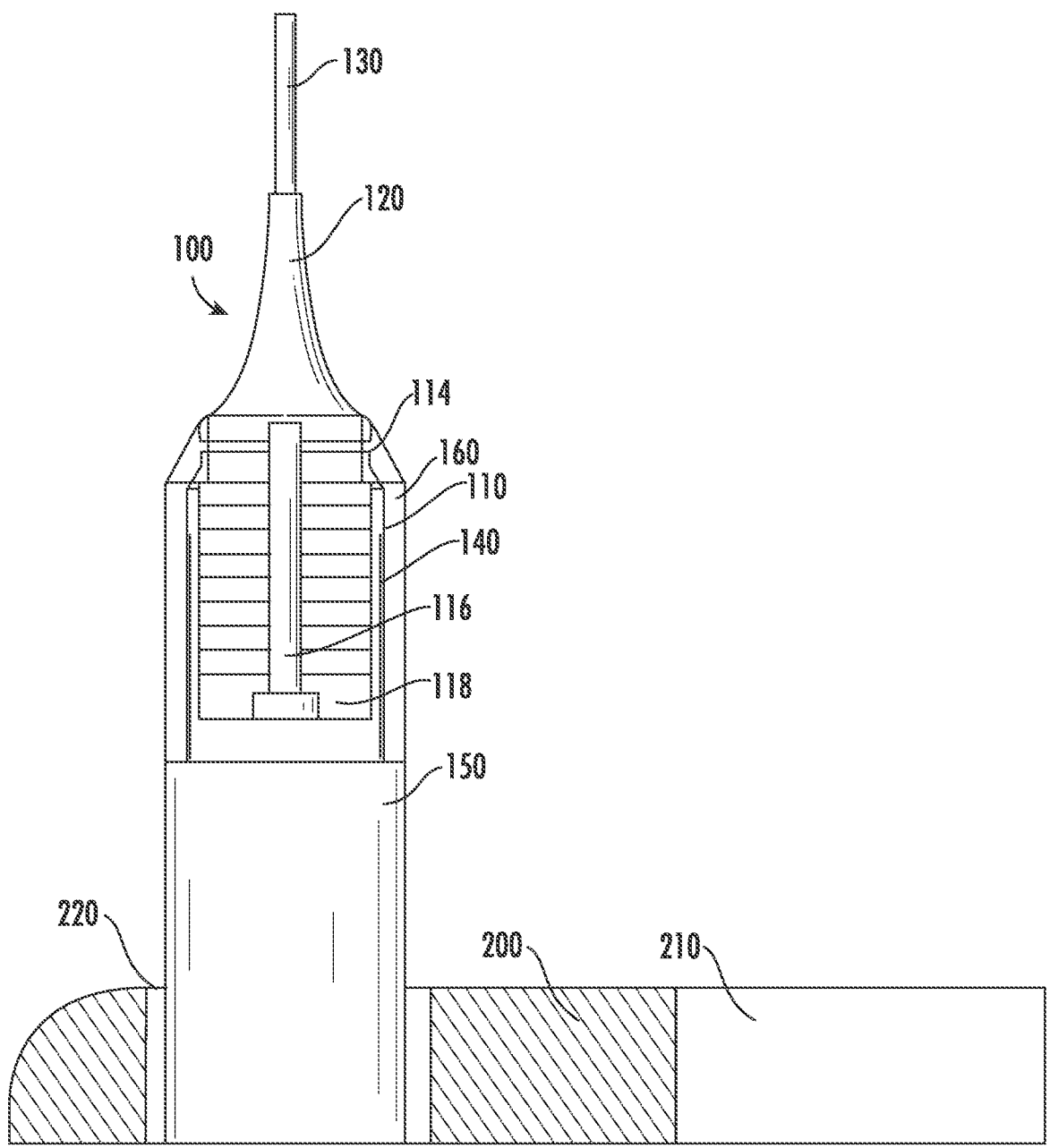
FIG. 1B is a schematic partial cross-sectional view of a distal portion of an ultrasonic treatment device in accordance with the present disclosure, extending from a working channel of an endoscope, in accordance with the present disclosure.
Figure 2:
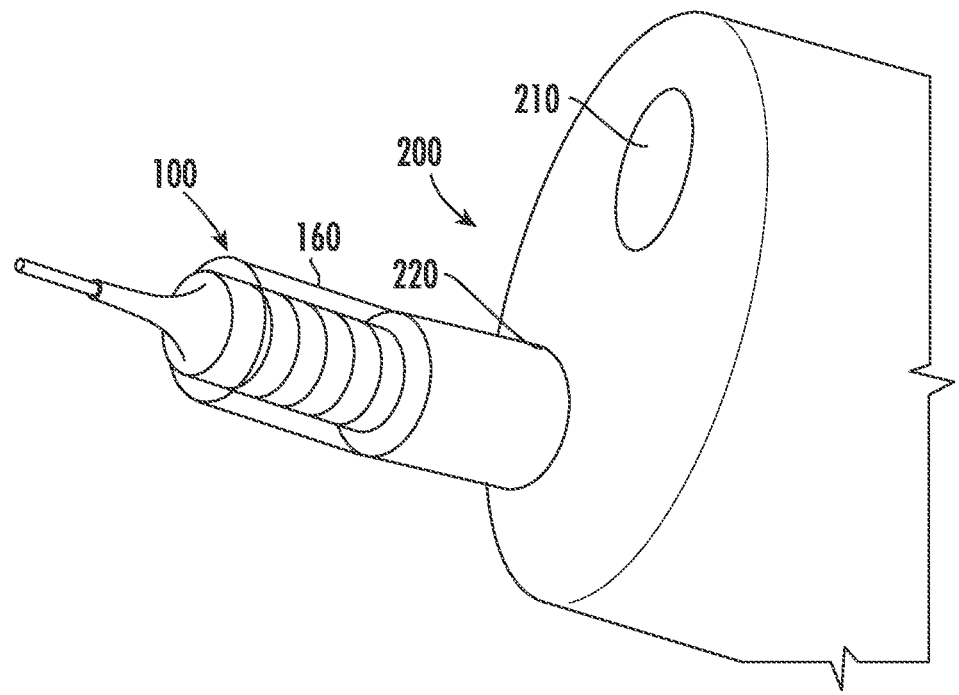
FIG. 2 is a schematic perspective view of a distal portion of an ultrasonic treatment device in accordance with the present disclosure, extending from a working channel of an endoscope, in accordance with the present disclosure.

For example, with reference to FIG. 1B and FIG. 2, there is schematically shown therein a distal end of an ultrasonic treatment device that includes an effector assembly 100 disposed at a distal end of a flexible shaft 150 having an internal channel (not shown) which encloses a plurality of flexible electrical conductors 140 as well as any optional supplemental members, for example, one or more control members as described below. Suitable materials for the flexible shaft include metallic and polymeric shaft materials. For example, the flexible shaft may be formed from polymer such as polyether block amide (PEBAX), polycarbonate, acrylonitrile butadiene styrene (ABS), nylon, for instance, nylon 6 or nylon 12, polyurethane and/or fluoropolymers such as polytetrafluoroethylene (PTFE) or fluorinated ethylene propylene (FEP), among others. Moreover, the flexible shaft may be reinforced with polymeric or metallic (e.g., stainless steel, nitinol, etc.) elements to provide torque control. The flexible shaft may be, for example, in the form of a tube or may be reinforced, for instance, using one or more helically coiled filaments or ribbons (including braided structures), longitudinally spaced rings, annular corrugation, helical corrugation or stripwound reinforcement structures. The flexible shaft may be configured to bend at bending angles, for example, having a bending radius of less than 25 mm, less than 15 mm, or even less than 10 mmm, among other possibilities. The effector assembly 100 and a distal portion of the flexible instrument shaft 150 extend from a working channel 220 of an endoscope 200 in the embodiment shown in FIGS. 1B and 2. The endoscope 200 further comprises endoscope optics 210, which are disposed in another channel of the endoscope 200.

The effector assembly 100 shown includes a piezoelectric transducer 110 which comprises a stack of piezoceramic disks which are held in compression between a distal face of a compression member 118 and a proximal face of an amplification device 120 (in the form of an acoustic horn) by a compression rod 116, thereby reducing the amount of energy required to activate the piezoelectric disks. It is noted that, in some cases, the effector assembly may comprise a separate plate (which is not the amplification device), attached to the amplification device. A distal end of the amplification device 120 terminates at a proximal end of the end effector 130. Flexible electrical conductors 140 are in electrical communication with the piezoelectric transducer 110 at a distal end of the device and in electrical communication with and electrical generator (not shown) at another end (i.e., a proximal end), which electrical generator generates ultrasonic control signals which drive the piezoelectric transducer 110, and thus the end effector 130, at an ultrasonic frequency.

Suitable materials for the piezoceramic disks include, for example, lead zirconate titanate (Pb[Zr$_x$Ti$_{1-x}$]O$_3$ 0≤x≤1), commonly known as PZT, Pb$_2$KNb$_5$O$_{15}$, barium titanate (BaTiO$_3$), Ba$_2$NaNb$_5$O$_5$, potassium niobate (KNbO$_3$), lithium niobate (LiNbO$_3$), lithium tantalate (LiTaO$_3$), sodium tungstate (Na$_2$WO$_3$), and/or zinc oxide (ZnO)—Wurtzite structure, among other possibilities. Suitable materials for the compression rod include, for example, metals such as 17-4 stainless steel, 316 stainless steel and titanium, among other possibilities. Suitable materials for the compression member 118 include, for example, metals such as aluminum (e.g., anodized aluminum), 17-4 stainless steel, 316 stainless steel and titanium, among other possibilities. Suitable materials for the amplification device 120 include, for example, metals such as aluminum (e.g., anodized aluminum), 17-4 stainless steel, 316 stainless steel and titanium, among other possibilities.

In the embodiment shown, the transducer is enclosed within a transducer housing 160. To reduce transmission of ultrasonic vibration to the transducer housing 160, the transducer assembly 100 may be mounted in the transducer housing 160 using non-rigid connectors in at least one location. Such non-rigid connections may act to mechanically link the effector assembly 100 to the transducer housing 160, while at the same time allowing the transducer to vibrate ultrasonically almost independently from the transducer housing 160. These non-rigid connections may be in the form of circumferential or semi-circumferential bands of elastic material (e.g., rubber, silicone, thermoplastic elastomer, etc.). In the embodiment shown, a non-rigid connector in the form of a ring-like transistor mounting 114 is provided, which acts as a vibration-damping mechanical link between the effector assembly 100 (more specifically, a proximal end of the amplification device 120) and the transducer housing 160. In some embodiments, an optional circulation system (not shown) for circulating a cooling gas (e.g., air, oxygen, nitrogen, helium, etc.) may be used in the transducer housing to cool the transducer. This gas circulation system may include at least one lumen (e.g., a supply lumen and, optionally a return lumen) that connects the transducer housing to a source of gas pressure or a vacuum source, in order to move a cooling gas through the transducer housing.

In various embodiments, the effector assembly may be positioned at a distal end of a flexible endoscope body.

Figure 3:
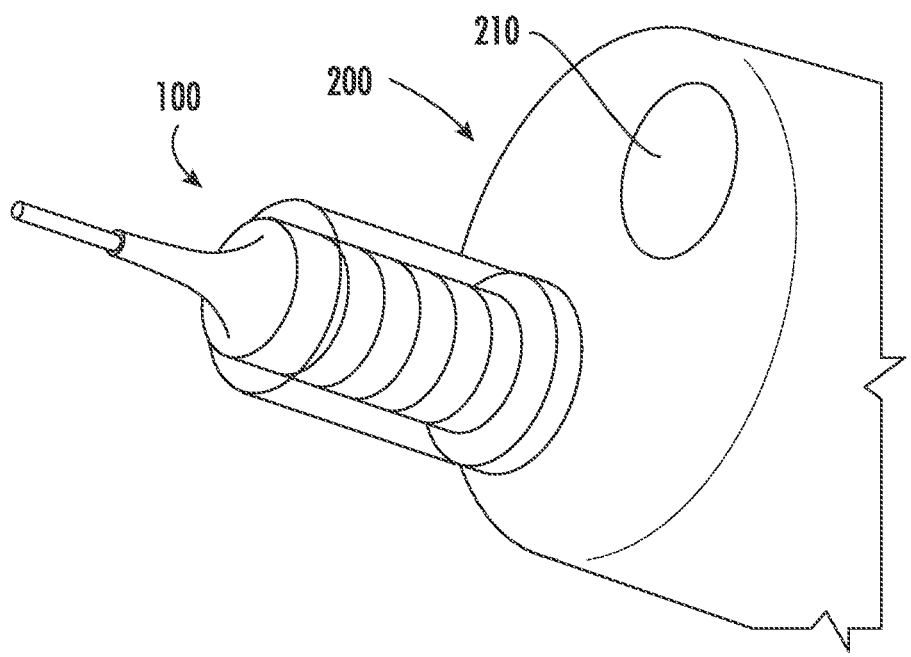
FIG. 3 is a schematic perspective view of a distal portion of an ultrasonic treatment device in accordance with the present disclosure, back-fed into a lumen of an endoscope, in accordance with the present disclosure.

For example, in some embodiments, the effector assembly of the ultrasonic treatment device that includes may be positioned at the distal end of a flexible endoscope body as a back-fed attachment. Referring now to FIG. 3, there is schematically shown a distal end of an ultrasonic treatment device that includes an effector assembly 100 and associated housing 160 disposed at a distal end of an endoscope 200. The effector assembly 100 includes a piezoelectric transducer, compression rod, compression member, amplification device, and end effector as previously described. In the embodiment shown, effector assembly 100 is larger in diameter than the endoscope lumen that it occupies, which is an advantage of using a back-fed system. In this case no separate flexible shaft (such as flexible instrument shaft 150 of FIGS. 1B and 2) is required, as the flexible electrical conductors (as well as any additional members, for example, one or more control members as described below) can be fed through a working channel of the endoscope 200. As in FIG. 1B and FIG. 2, the endoscope 200 further comprises endoscope optics 210, which are disposed in another channel of the endoscope 200.

Figure 4:
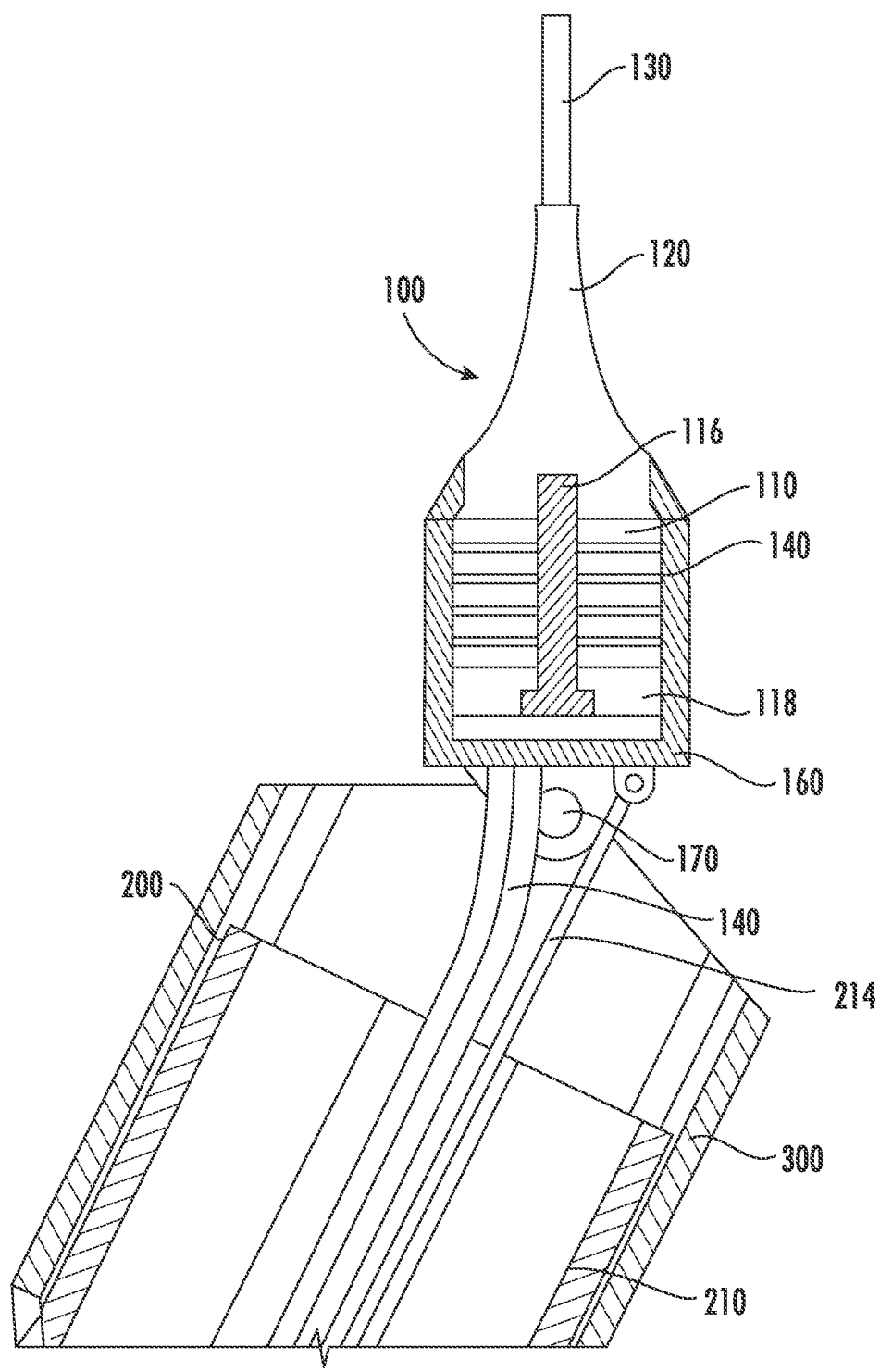
FIG. 4 is a schematic cross-sectional view of a distal portion of an ultrasonic treatment device in accordance with the present disclosure, pivotably attached to a cap which is, in turn, attached to a distal end of an endoscope, in accordance with the present disclosure.
Figure 5:
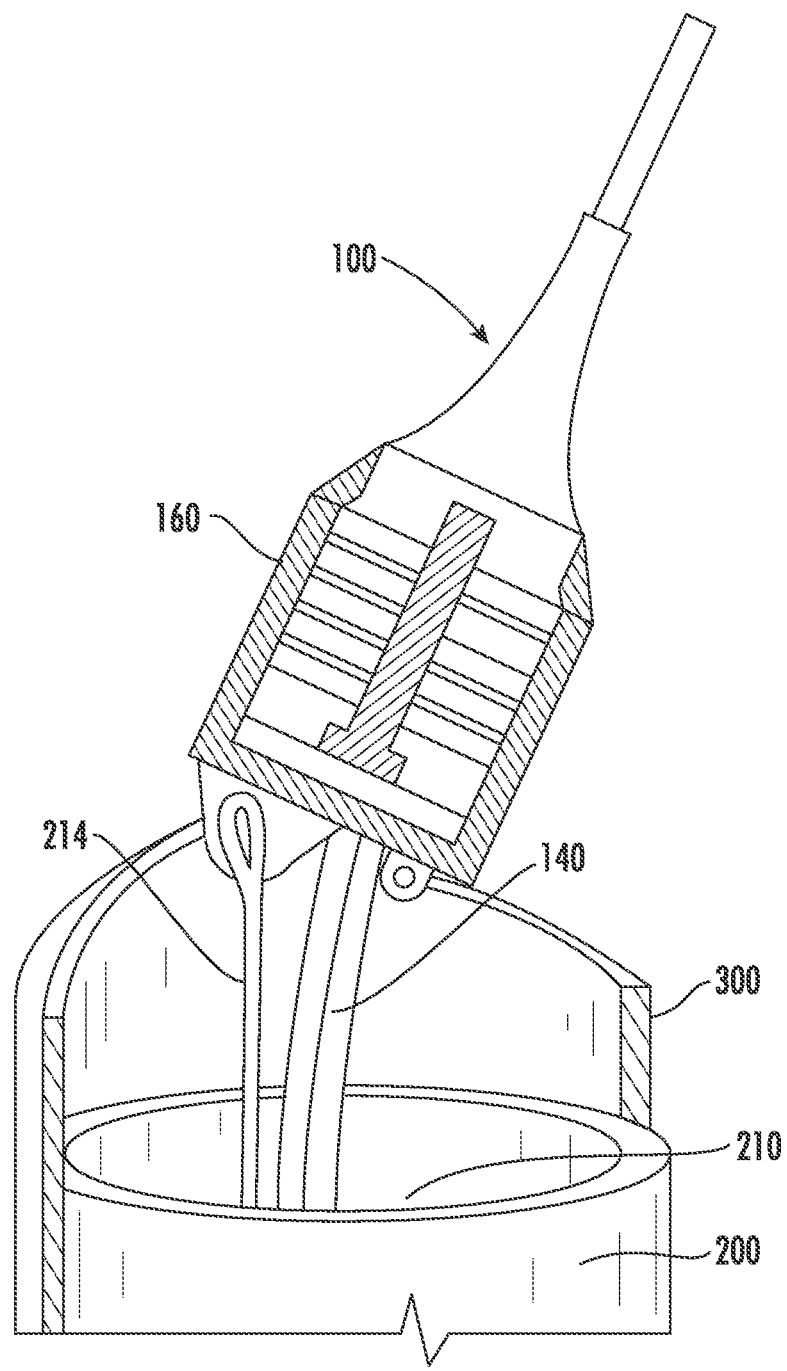
FIG. 5 is a schematic perspective view of a distal portion of an ultrasonic treatment device in accordance with the present disclosure, which is pivotably attached to a cap that is, in turn, attached to a distal end of an endoscope, wherein flexible electrical conductors and articulation control are fed inside the endoscope, in accordance with the present disclosure.

As another example, in some embodiments, the effector assembly of the ultrasonic treatment device may be positioned at the distal end of a flexible endoscope body as a cap which is attached to, inserted into, or fit over the distal end of the flexible endoscope body. Referring now to FIGS. 4 and 5, there is schematically shown a distal end of an ultrasonic treatment device that includes an effector assembly 100 and associated housing 160 attached to a cap 300, which is disposed at a distal end of an endoscope 200. The housing 160 is attached to the cap 300 in a pivotable fashion in the embodiment shown via a hinged joint 170. The effector assembly 100 includes a piezoelectric transducer 110, compression rod 116, compression member 118, amplification device 120 and end effector 130 as previously described. Flexible electrical conductors 140 are in electrical communication with the piezoelectric transducer 110 at one end and in electrical communication with an electrical generator (not shown) at another end, which electrical generator generates ultrasonic control signals which drive the piezoelectric transducer 110, and thus the end effector 130, at an ultrasonic frequency. The flexible electrical conductors 140 are fed through a lumen of the endoscope 200 in the embodiment shown.

With a distal transducer location, articulation capabilities are possible, in which articulation features may be located proximal to the distal end of the transducer (including within the transducer housing), keeping the transducer in line with the distal tool during articulation. In various embodiments, an effector assembly is provided, which includes an articulation portion positioned proximal to the effector assembly and an articulation control.

In the embodiment shown in FIGS. 4 and 5, a hinged joint 170 acts an articulation portion. The housing 160 is attached to the cap 300 in a pivotable fashion via the hinged joint 170. More broadly, a wide range of articulation portions may be employed in addition to a joint, including a link, a flexible segment such as a corrugated segment or a slotted segment, or a pre-bent (e.g., heat-set, etc.) segment having a memorized shape that it can return to after straightening.

In the embodiment shown in FIGS. 4 and 5, a control rod 214 fed through a working channel 210 of the endoscope 200 acts as an articulation control for the user. More broadly, a wide range of elongate articulation controls may be employed in addition to a control rod/wire including a stiff tubular member or an oversheath. In the case of a pre-bent segment, the degree of bending may be changed, for example, via a stiff linear inner member that can be positioned within an internal lumen of the pre-bent segment or via a stiff linear outer member that is inserted over the pre-bent segment (i.e., the pre-bent segment is positioned with a lumen of the outer member). In either case, when the stiff linear inner or outer member is positioned within or over the pre-bent segment, the pre-bent segment is forced to take on a substantially linear configuration. Withdrawal of the stiff linear inner or outer member relative to the pre-bent segment, on the other hand, allows the pre-bent segment to regain its memorized shape.

Figure 6:
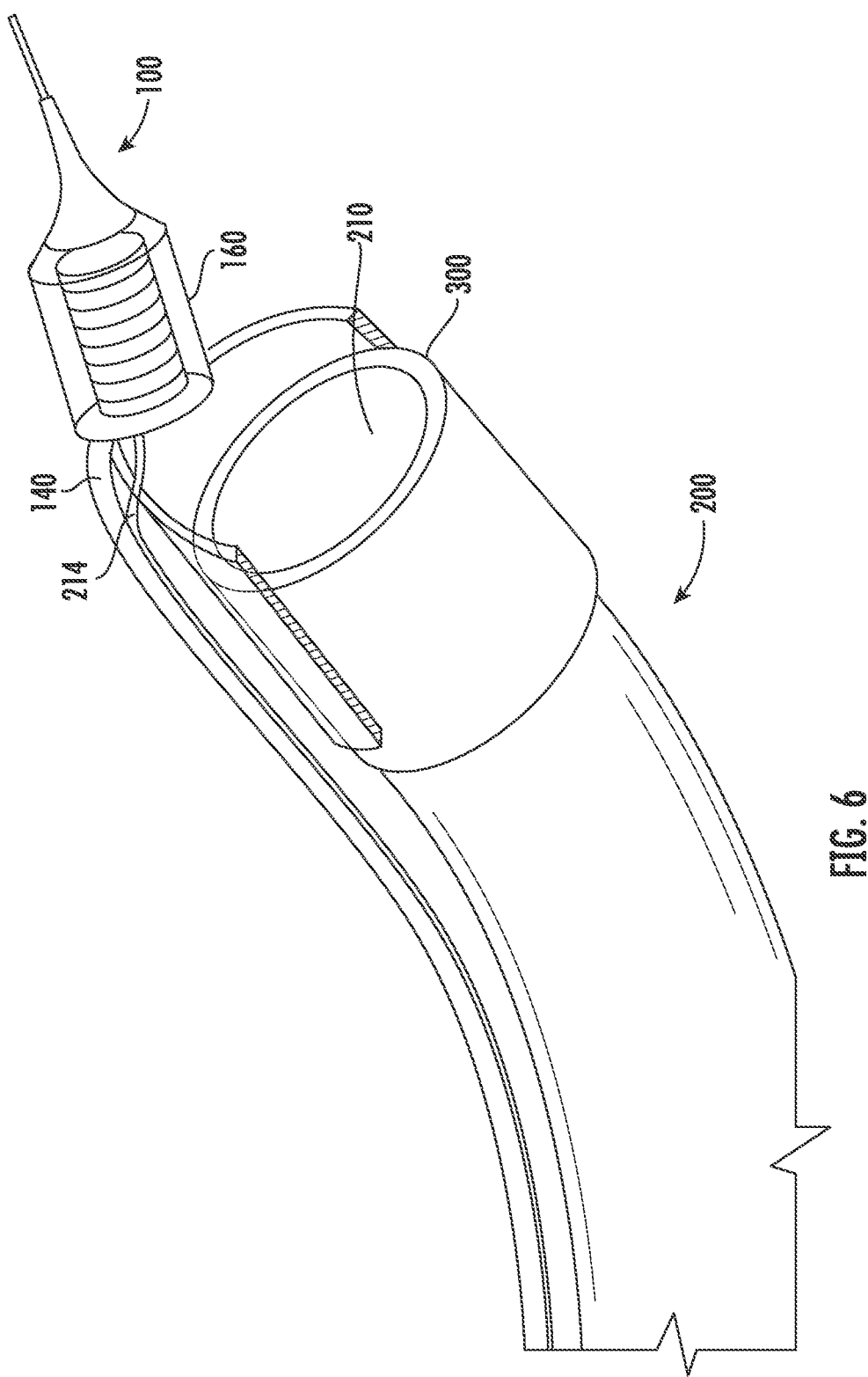
FIG. 6 is a schematic perspective view of a distal portion of an ultrasonic treatment device in accordance with the present disclosure, which is pivotably attached to a cap that is, in turn, attached to a distal end of an endoscope, wherein flexible electrical conductors and articulation control are fed outside the endoscope, in accordance with the present disclosure.

The flexible electrical conductors and articulation control may be fed through the working channel (see, e.g., FIG. 5) or other lumen (see, e.g., FIG. 4) of the endoscope. Alternatively, the articulation control may be fed outside the scope, optionally, in an auxiliary lumen (e.g., a separate sheath). One such embodiment is schematically shown in FIG. 6 wherein an effector assembly 100 and associated housing 160 are attached to a cap 300, which is disposed at a distal end of an endoscope 200. As above, flexible electrical conductors 140 are in electrical communication with the piezoelectric transducer 110 at one end and in electrical communication with an electrical generator (not shown) at another end, and an articulation control 214 (control rod) acts as an articulation control for the user. However, in this case, the flexible electrical conductors 140 and articulation control 214 are fed outside the endoscope 200. The effector assembly 100 and optics 210 are off-center as shown, thereby minimizing the ability of the effector assembly 100 to obstruct the optics 210.

In cases where the transducer and end effector are attached over the scope, an electrical connection point and/or fluid connection point may be located between the transducer and the operator to allow a source of electrical current to be disconnected and reconnected, to allow a source of cooling fluid to be disconnected and reconnected, or both. Such a connection may be made distal to the endoscope, proximal to the endoscope or at some point along the endoscopy length.

Figure 7A:
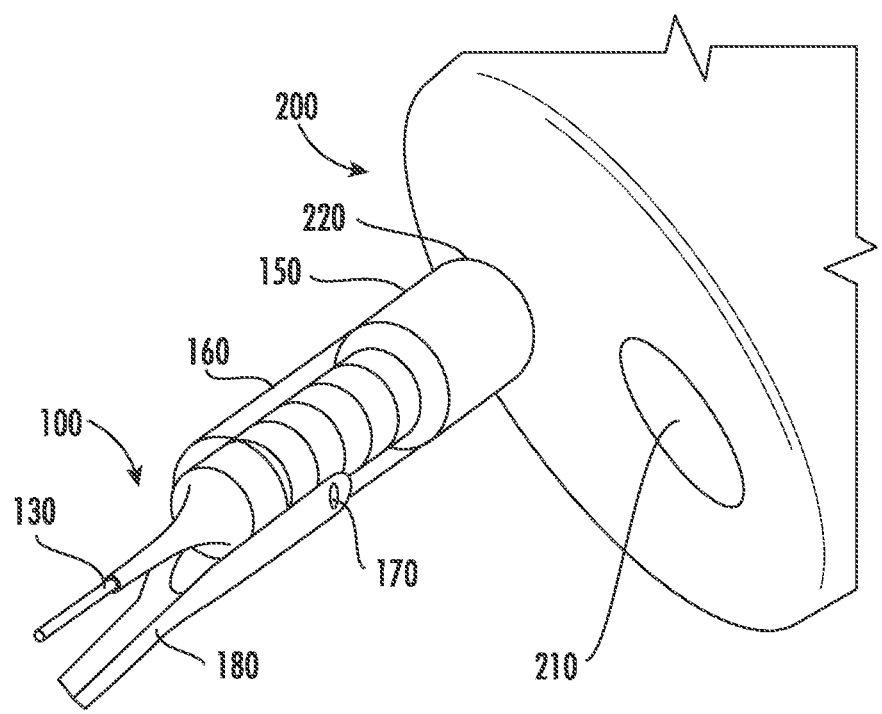
FIG. 7A and FIG. 7B are schematic perspective views of a distal portion of an ultrasonic treatment device with an actuatable arm in accordance with the present disclosure, extending from a working channel of an endoscope, wherein the actuatable arm is in open and closed positions, respectively, in accordance with the present disclosure.
Figure 7B:
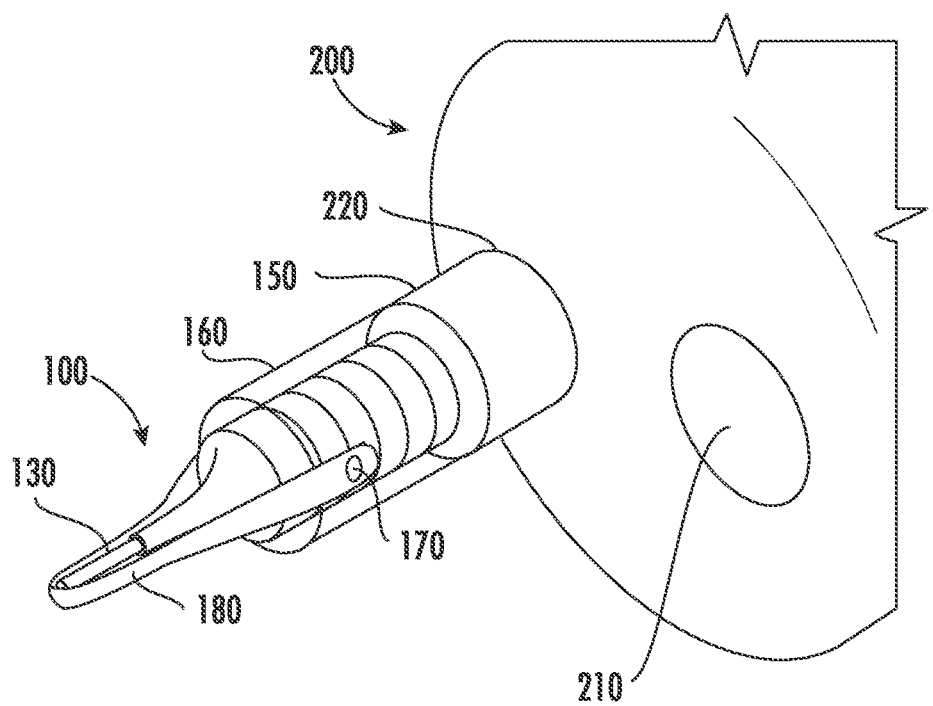

In various embodiments, an ultrasonic treatment device in accordance with the present disclosure further comprises an actuatable arm configured to press tissue against the end effector. One specific example of such an actuatable arm is illustrated schematically in FIGS. 7A and 7B, which shows an endoscope 200 comprising a working channel 220 and optics 210 which are disposed another channel of the endoscope 200. An ultrasonic treatment device in accordance with the present disclosure, which comprises an effector assembly 100 disposed at a distal end of a flexible shaft 150, is inserted through the channel 220 of the endoscope 200 in the embodiment shown. The effector assembly 100 and the distal end of the flexible shaft 150 are shown extending from the working channel 220. The effector assembly 100 in the embodiment shown further includes an actuatable arm 180 which is actuatable between an open position as shown in FIG. 7A and a closed position as shown in FIG. 7B, wherein the actuatable arm 180 engages the end effector 130 portion of the effector assembly 100. The actuatable arm 180 pivots via hinged joints 170 disposed in the housing 160. The actuatable arm 180 may be controlled by any of a wide range of elongate control members (not shown), for example, an elongate control element such as a filament, wire, rod, tubular member, or an oversheath as described above, which extend from a proximal end of the actuatable arm 180 to a proximal end of the endoscope (not shown), allowing a health care professional to actuate the arm 180. In certain embodiments, the end effector 130 may be provided with different faces (not shown) which can be oriented toward or away from the actuatable arm 180, for example, by rotating the end effector 130 independently from the actuatable arm 180. In this way different features on the end effector 130 may interface with the actuatable arm 180.

In other aspects, the present invention provides an endoscopic system comprising: (a) an ultrasonic treatment device like that described above and (b) a control unit comprising an electrical generator that is configured to generate ultrasonic control signals. In various embodiments, the control unit may further comprise a user interface, which may allow a user to input information (e.g., via buttons, dials, keypad, mouse, touchscreen, etc.). The control unit may further include an activation mechanism that can be operated by the user hand or foot (e.g., foot switch, trigger, etc.), which allows the user to turn the piezoelectric transducer on and off and, optionally, to control the intensity of the transducer vibrations. Moreover, the electrical signal may be transferred through flexible electrical conductors along a flexible path, for example, routed into a body of a patient through a port, guide, endoscope, or natural orifice to a target site. In certain embodiments, the flexible electrical conductors may be disposed within an endoscope lumen, for example, through a working channel or other suitable lumen of an endoscope (optionally, in a separate sheath) or through flexible electrical conductors disposed alongside an endoscope (also optionally, in a separate sheath), among other possibilities.

In such aspects, the system may thus comprise (a) proximal elements, including, for example, a generator, user interface and activation mechanism, disposed outside the body of a patient, (b) distal elements, including, for example, a piezoelectric transducer, housing, amplifier, and end effector, disposed within the body, and (b) a flexible elongate conductor crossing into the body of the patient, disposed between the proximal elements and distal elements.

The invention claimed is:

1. An ultrasonic treatment device comprising:
   (a) a flexible elongate body having a proximal end and a distal end;
   (b) an effector assembly disposed at the distal end of the flexible elongate body, the effector assembly comprising a piezoelectric transducer, an end effector and an actuatable arm connected to the end effector, wherein the piezoelectric transducer comprises a stack of piezoceramic disks held within a transducer housing between a compression member and an amplification device by a compression rod, wherein the end effector is rotatable about a longitudinal axis of the flexible elongate body independent of the actuatable arm, and wherein the actuatable arm is pivotally attached to an outer surface of the transducer housing and configured to engage the end effector to press tissue against the end effector; and
   (c) flexible electrical conductors in electrical communication with the piezoelectric transducer, the flexible electrical conductors extending along a length of the flexible elongate body, wherein the flexible elongate body is configured for insertion to a target site within a patient, and wherein the piezoelectric transducer transfers electrical energy to mechanical motion at the target site.

2. The ultrasonic treatment device of claim 1, wherein the effector assembly further comprises a piezoelectric amplifier disposed between and mechanically linking the piezoelectric transducer and the end effector.

3. The ultrasonic treatment device of claim 1, wherein the ultrasonic treatment device is an ultrasonic cutting device.

4. The ultrasonic treatment device of claim 1, further comprising a generator configured to send electrical signals to the piezoelectric transducer.

5. The ultrasonic treatment device of claim 1, wherein the flexible elongate body is configured for insertion through a working channel of an endoscope.

6. The ultrasonic treatment device of claim 1, wherein the end effector comprises a rod, a ball, a hook or a cutting tool, or a combination thereof.

7. The ultrasonic treatment device of claim 1, wherein the actuatable arm pivots via hinged joints disposed in the transducer housing.

8. The ultrasonic treatment device of claim 1, wherein the flexible elongate body is an endoscope body.

9. The ultrasonic treatment device of claim 8, wherein the effector assembly is attached to a distal end of the endoscope body as a cap or wherein the effector assembly is inserted into a lumen at a distal end of the endoscope body.

10. The ultrasonic treatment device of claim 8, wherein the effector assembly further comprises (i) an articulation portion positioned at the distal end of the flexible elongate body, and (ii) an articulation control extending proximally from the articulation portion.

11. The ultrasonic treatment device of claim 10, wherein the articulation portion comprises a joint, a link, a flexible segment, a corrugated segment, a slotted segment or a pre-bent segment with shape memory, or a combination thereof.

12. The ultrasonic treatment device of claim 10, wherein the articulation control comprises a wire, a rod or a sheath, or a combination thereof.

13. An endoscopic system comprising:
(a) a control unit comprising an electrical generator configured to generate ultrasonic control signals;
(b) a flexible elongate body;
(c) an effector assembly disposed at a distal end of the flexible elongate body, the effector assembly comprising a piezoelectric transducer, an end effector and an actuatable arm connected to the end effector, wherein the piezoelectric transducer comprises a stack of piezoceramic disks held within a transducer housing between a compression member and an amplification device by a compression rod, wherein the end effector is rotatable about a longitudinal axis of the flexible elongate body independent of the actuatable arm, and wherein the actuatable arm is pivotally attached to an outer surface of the transducer housing and configured to engage the end effector to press tissue between the actuatable arm and the end effector; and
(d) flexible electrical conductors configured to provide electrical communication between the control unit and the piezoelectric transducer, wherein the flexible elongate body is configured for insertion to a target site within a patient, and wherein the piezoelectric transducer transfers electrical energy to mechanical motion at the target site.

14. The endoscopic system of claim 13, wherein the control unit further comprises one or both of (a) a user interface, and (b) a hand-operated or foot-operated mechanism configured to activate and deactivate the piezoelectric transducer.

15. The endoscopic system of claim 13, wherein the flexible elongate body is configured for insertion through a working channel of an endoscope.

16. The endoscopic system of claim 13, wherein the flexible elongate body is an endoscope body.

17. The endoscopic system of claim 16, wherein the flexible electrical conductors are disposed alongside the endoscope body.

18. A method of treatment, comprising:
inserting an ultrasonic treatment device into a patient; and
treating target tissue at a target site in the patient with said ultrasonic treatment device;
wherein the ultrasonic treatment device comprises:
(a) a flexible elongate body having a proximal end and a distal end,
(b) an effector assembly disposed at the distal end of the flexible elongate body, the effector assembly comprising a piezoelectric transducer an end effector and an actuatable arm connected to the end effector, wherein the piezoelectric transducer comprises a stack of piezoceramic disks held within a transducer housing between a compression member and an amplification device by a compression rod, wherein the end effector is rotatable about a longitudinal axis of the flexible elongate body independent of the actuatable arm, and wherein the actuatable arm is pivotally attached to an outer surface of the transducer housing and configured to engage the end effector to press tissue against the end effector, and
(c) flexible electrical conductors in electrical communication with the piezoelectric transducer, the flexible electrical conductors extending along a length of the flexible elongate body, wherein the piezoelectric transducer transfers electrical energy to mechanical motion at the target site.

* * * * *